United States Patent
Zhong et al.

(10) Patent No.: US 10,179,331 B2
(45) Date of Patent: Jan. 15, 2019

(54) LIGAND BASED CHROMIUM CATALYST AND APPLICATION IN CATALYZING ETHYLENE OLIGOMERIZATION

(71) Applicants: CHINA PETROLEUM & CHEMICAL CORPORATION, Beijing (CN); XIAMEN UNIVERSITY, Xiamen (CN); SHANGHAI RESEARCH INSTITUTE OF CHEMICAL INDUSTRY, Shanghai (CN)

(72) Inventors: Xianghong Zhong, Maoming (CN); Hongping Zhu, Xiamen (CN); Xiaofeng Ye, Shanghai (CN); Yucai Cao, Shanghai (CN); Shengbiao Liang, Maoming (CN); Zhenyu Liu, Maoming (CN); Shumeng Xiao, Maoming (CN); Rui Liu, Xiamen (CN); Yanfang Huang, Maoming (CN); Jiancheng Li, Xiamen (CN)

(73) Assignees: CHINA PETROLEUM & CHEIMCAL CORPORATION, Beijing (CN); XIAMEN UNIVERSITY, Xiamen (CN); SHANGHAI RESEARCH INSTITUTE OF CHEMICAL INDUSTRY, Shanghai (CN)

( * ) Notice: Subject to any disclaimer, the term of this patent is extended or adjusted under 35 U.S.C. 154(b) by 0 days.

(21) Appl. No.: 15/297,904

(22) Filed: Oct. 19, 2016

(65) Prior Publication Data

US 2017/0106358 A1 Apr. 20, 2017

(30) Foreign Application Priority Data

Oct. 19, 2015 (CN) .......................... 2015 1 0674794

(51) Int. Cl.
*B01J 31/24* (2006.01)
*B01J 31/14* (2006.01)
*C07C 2/36* (2006.01)
*C07C 2/26* (2006.01)

(52) U.S. Cl.
CPC ......... *B01J 31/2409* (2013.01); *B01J 31/143* (2013.01); *C07C 2/26* (2013.01); *C07C 2/36* (2013.01); *B01J 2231/20* (2013.01); *B01J 2531/62* (2013.01); *C07C 2531/14* (2013.01); *C07C 2531/24* (2013.01)

(58) Field of Classification Search
None
See application file for complete search history.

(56) References Cited

U.S. PATENT DOCUMENTS 5,550,305 A 8/1996 Wu
5,811,618 A 9/1998 Wu

FOREIGN PATENT DOCUMENTS

| CN | 102585054 A | 11/2013 |
| EP | 1574492 A2 | 9/2005 |
| WO | 2003/053891 A1 | 7/2003 |

OTHER PUBLICATIONS

Alzamly et al. Organometallics, 2013, 32, 7204-7212 (Year: 2013).*
Liu et al. Chinese Journal of Organic Chemistry, 2013, 33, 808-814 (Year: 2013).*
Bluhm et al. (Journal of Organometallic Chemistry, 690, 713-721 (Year: 2005).*
Search Report dated May 3, 2017 for Netherlands Patent Application No. 2017640.

* cited by examiner

*Primary Examiner* — Yun Qian
(74) *Attorney, Agent, or Firm* — Duane Morris LLP

(57) ABSTRACT

A ligand based chromium catalyst and application in catalyzing ethylene oligomerization are disclosed. The chromium catalyst is formed by a chromium compound and an organic ligand containing P and/or N. The substituents on N and P of the ligand can be replaced, whereby selective ethylene trimerization and tetramerization can be realized so as to produce 1-hexene and 1-octene at the same time.

23 Claims, 1 Drawing Sheet

LIGAND BASED CHROMIUM CATALYST AND APPLICATION IN CATALYZING ETHYLENE OLIGOMERIZATION

CROSS REFERENCE TO RELATED APPLICATION

The present application claims priority to Chinese patent application CN 201510674794.4, filed on Oct. 19, 2015, the entirety of which is incorporated herein by reference.

FIELD OF THE INVENTION

The present disclosure relates to a ligand based chromium catalyst and its application in catalyzing ethylene oligomerization.

BACKGROUND OF THE INVENTION

The selective oligomerization of ethylene provides a vital route to the production of specific linear alpha-olefins (LAO), and is an important technological research task in olefin polymerization and catalysis field. Among the linear alpha-olefins, 1-hexene and 1-octene have become important comonomer for production of linear low density polyolefin (LLDPE). Compared with polyethylene, multiple performances of the polyolefin products, which are produced with 1-hexene and 1-octene as the comonomer, can be significantly improved, such as mechanical performance, optical performance, tearing resistance strength, and impact resistance strength. The polyolefin products can be used as film materials, and have a wide use and a large demand in industrial production.

In traditional ethylene oligomerization reaction, aluminum-based catalyst, titanium-based catalyst, nickel-based catalyst, zirconium-based catalyst, iron-based catalyst, or cobalt-based catalyst are used. The reaction mainly follows the Cossee-Arlman mechanism. That is, ethylene proceeds with linear chain-growth in the presence of the metal catalyst, and then proceeds with chain-elimination by β-hydrogen migration, thereby generating linear alpha-olefins. During the reaction procedure, the chain-growth rate is slightly larger than or roughly equal to the chain-elimination rate. Therefore, the carbon chain grows within a certain limit, and the number of carbon atoms mainly ranges from 4 to 30, and the alpha-olefin products generated therein are in consistent with Schulz-Flory or Poisson distribution. The content of 1-hexene and 1-octene in the products is relatively low (J. Organomet. Chem. 2004, 689, 3641). U.S. Pat. No. (3,676, 523) discloses a Shell Higher Olefin Process (SHOP) for producing alpha-olefins using nickel-based catalyst, and the content of $C_6$ to $C_{10}$ olefins in the alpha-olefin products ranges from 21.0% to 52.0%. A oligomerization product under a catalytic effect of an iron-based catalyst is reported by Brookhart et al, wherein the content of $C_6$ and $C_8$ olefins ranges from 47% to 52% (J. Am. Chem. Soc., 1998, 120, 7143; U.S. Pat. No. 6,103,946).

The selective oligomerization reaction of ethylene is a subsequently developed method, which has a very important application prospect and an important role in industrial synthesis of specific linear alpha-olefins. The production of 1-hexene through selective trimerization of ethylene is firstly discovered by Union Carbide Corporation (U.S. Pat. No. 3,300,458). In 1999, the catalytic reaction for ethylene trimerization using a system of 2-ethylhexanoate chromium, 2,5-dimethylpyrrole, triethylaluminum, and diethylaluminum chloride in cyclohexane solvent under a temperature being 115° C. and a pressure being 100 bar is reported by Phillips. The reaction has a high selectivity, 1-hexene accounts for 93% of the products, and an activity of the catalyst reaches $1.56 \times 10^5$ g/(g Cr·h) (U.S. Pat. No. 5,856, 612). In 2002, the catalytic reaction for trimerization of ethylene using a system of chromium trichloride, PNP-ligand, and methylaluminoxane in toluene solvent under a temperature being 80° C. and a pressure being 20 bar is reported by British Petroleum (BP). The reaction also has a high selectivity, 1-hexene accounts almost for 90% of the products, and an activity of the catalyst reaches $1.03 \times 10^6$ g/(g Cr·h). Besides, the reaction condition is relatively mild (Chem. Commun. 2002, 858; U.S. Pat. No. 5,856,612). In 2004, based on the research of British Petroleum, the aryl substituent on the phosphorus atom of the PNP-ligand, i.e., the methoxyl is replaced to be H or alkyl group by researchers of Sasol limited, and the new ligand forms a system with chromium trichloride and methylaluminoxane. The catalytic reaction for ethylene tetramerization is then performed using the aforesaid system in toluene solvent under a temperature being 65° C. and a pressure being 30 bar or under a temperature being 45° C. and a pressure being 45 bar. 1-octene accounts for 70% of the products, and an activity of the catalyst ranges from $8.05 \times 10^3$ g/(g Cr·h) to $4.36 \times 10^4$ g/(g Cr·h). Then, various replacements of substituents on phosphorus atom and nitrogen atom are performed, and the catalytic results of selective tetramerization of ethylene obtained therein are similar to the above result (J. Am. Chem. Soc., 2004, 126, 14712; WO 056478).

The catalytic reaction mechanism of selective trimerization of ethylene is different from the Cossee-Arlman mechanism of linear chain growth. The catalytic reaction for selective trimerization of ethylene mainly follows a metal cyclization reaction mechanism. That is, ethylene molecules are trimerized in the presence of the metal catalyst to form a $CrC_6$ seven-membered ring intermediate compound, and then form hexane after intra-ring β-H migration and reduction elimination reaction. During selective tetramerization of ethylene, an ethylene molecule is inserted into the $CrC_6$ seven-membered ring intermediate so as to form a $CrC_8$ nine-membered ring intermediate compound, and then form octane after intra-ring β-H migration and reduction elimination reaction. The selective tetramerization of ethylene is relatively difficult, because the $CrC_8$ nine-membered ring intermediate has a poor structural stability compared with the $CrC_6$ seven-membered ring intermediate. However, the selective tetramerization of ethylene can be realized through electronic and steric structural regulation on the ligand around Cr of the catalyst, which is fully recognized by the researchers in the art. Nevertheless, related work is done very little.

At present, the industrial directional production of 1-hexene is realized by selective trimerization of ethylene. For example, Phillips successfully built a 1-hexene production equipment in Qatar during 2003. The product of this equipment is single, and the selectivity of 1-hexene reaches 90% or above. Besides, the production equipment has less by-products, a high catalytic activity, and a simple work flow. The 1-hexene production equipment through selective trimerization of ethylene in Daqing Petrochemical Company in China is already put into production, and the similar equipment in Yanshan Petrochemical Company in China is about to be put into production. The industrial production of 1-octene is about to be realized by selective tetramerization of ethylene, but there are still theoretical and technological difficulties in this respect.

SUMMARY OF THE INVENTION

The first purpose of the present disclosure is to provide a ligand based chromium catalyst.

A general formula of the ligand based chromium catalyst is as follows:

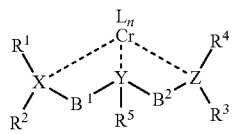

wherein in above structure, X, Y, and Z represent one element of N and P respectively, $R^1$, $R^2$, $R^3$, $R^4$, and $R^5$ represent one of H, linear or branched alkyl, heteroalkyl, cycloalkyl, heterocycloalkyl, substituted aryl and derivatives thereof respectively, $B^1$ and $B^2$ represent a structural system which can transmit an electronic induction or conjugative effect of a group respectively, and Ln represents a group which has a chemical bond with chromium; and wherein when X and Y both are N element, and Z is P element, $B^1$ represents one methylene group or a plurality of methylene groups. It is discovered that, when $B^1$ is selected to be one methylene group or a plurality of methylene groups, the catalytic ability of the ligand of regulating chromium to form $CrC_6$ and/or $CrC_8$ cyclic transition states and further form 1-hexene and/or 1-octene products can be significantly improved.

According to one preferred embodiment of the present disclosure, the chromium catalyst is formed by a chromium compound and an organic ligand containing P and/or N.

The chromium comes from a chromium inorganic compound or a chromium organic compound. The chromium inorganic compound is chromium dichloride or chromium trichloride. The chromium organic compound is one selected from a group consisting of chromium dichloride-tetrahydrofuran complex, chromium dichloride-toluene tetrahydrofuran complex, chromium trichloride-tetrahydrofuran (THF) complex, chromium dichloride-carbene complex, chromium trichloride-carbene complex, chromium acetylacetonate, chromium tris (2-ethylhexanoate), methyl chromium dichloride-tetrahydrofuran complex, triphenyl chromium-tetrahydrofuran complex, dimethyl chromium-carbene complex, diethyl chromium-carbene complex, diphenyl chromium-carbene complex, and carbonyl chromium.

The $R^1$, $R^2$, $R^3$, $R^4$, and $R^5$ groups, when being connected with nitrogen atom, are respectively one selected from a group consisting of H, $C_1$-$C_{10}$ linear or branched alkyl, heteroalkyl, or cycloalkyl, alkenyl, allyl, and substituted phenyl, preferably selected from a group consisting of H, methyl, ethyl, propyl, isopropyl, butyl, isobutyl, tert-butyl, pentyl, cyclobutyl, cyclopentyl, cyclohexyl, 2-methylcyclohexyl, 2,6-dimethylcyclohexyl, adamantly, vinyl, allyl, phenyl, naphthyl, 2-methylphenyl, 2,4-6-trimethylphenyl, 3,5-dimethylphenyl, 3,5-dimethoxyphenyl, 3,5-di-tert-butylphenyl, 2-thienyl, 2-furanyl, 2-pyridyl, and 3-pyridyl. The $R^1$, $R^2$, $R^3$, $R^4$, and $R^5$ groups, when being connected with phosphorus atom, are respectively one selected from a group consisting of $C_1$-$C_{10}$ linear or branched alkyl, substituted aryl, and derivatives thereof, preferably selected from a group consisting of methyl, ethyl, butyl, phenyl (which can be connected to be condensed nucleus compound), 2-methylphenyl, 4-methylphenyl, 3,5-dimethylphenyl, 2-methoxyphenyl, 4-methoxyphenyl, 3,5-dimethoxyphenyl, 4-tert-butylphenyl, 3,5-di-tert-butylphenyl, 2-nitrophenyl, 4-nitrophenyl, 4-cyanophenyl, 3,4-(methylenedioxy) phenyl, 4-benzoylphenyl, 4-ethoxycarbonylphenyl, 4-trifluoromethylphenyl, 1-naphthyl, 4,4'-biphenyl, 3,5-di(phenyl) phenyl, 2-thienyl, 2-furanyl, 2-pyridyl, and 3-pyridyl.

$B^1$ and $B^2$ represent a structural system which can transmit an electronic induction or conjugative effect of a group respectively. $B^1$ and $B^2$ can be the same as each other or different from each other. $B^1$ and $B^2$ are structural systems having two group bonds. $B^1$ and $B^2$ are respectively a double bond group containing 18 or less carbon atoms. In this manner, mutual electron transmission among atoms which has a ligand action with the catalyst metal element can be realized more effectively, so that the catalyst system can be stabilized and the catalytic activity thereof can be improved. Preferably, $B^1$ represents one methylene group or a plurality of methylene groups.

When the catalyst is used in an oligomerization action, the organic ligand containing P and/or N and the chromium compound can be mixed with each other in situ and used in the catalytic reaction, or a compound can be produced by the organic ligand containing P and/or N and the chromium compound through a chemical method and then used in the catalytic reaction.

The second purpose of the present disclosure is to provide an ethylene oligomerization method using the aforesaid catalyst.

The ethylene oligomerization method comprises performing ethylene oligomerization reaction in the presence of the catalyst according to the present disclosure in an organic solvent.

The oligomerization comprises selective trimerization and tetramerization of ethylene so as to obtain 1-hexene and 1-octene.

Specifically, the method further comprises the step of mixing the ligand based chromium catalyst with a co-catalyst in an organic solvent medium, so that the mixture contacts with olefin and oligomerization reaction is performed.

According to one embodiment of the present disclosure, in the method, a reaction temperature ranges from 0° C. to 200° C., an ethylene pressure ranges from 0.1 MPa to 20 MPa, a reaction time ranges from 0.01 h to 200 h, and a concentration of the catalyst ranges from 0.001 mmol/L to 1000 mmol/L.

According to one embodiment of the present disclosure, a ratio of the NP-ligand based chromium catalyst to the co-catalyst ranges from 1:10 to 1:4000, preferably ranges from 1:10 to 1:700.

The co-catalyst is at least one selected from a group consisting of alkyl aluminum compound, aluminoxane compound, and organic boron compound, preferably is at least one selected from a group consisting of triethylaluminum, triisobutylaluminum, tri-n-butylaluminium, tri-n-hexylaluminium, tri-n-octylaluminium, methylaluminoxane, ethylaluminoxane, isobutylaluminoxane and modified aluminoxane, methylaluminoxane loaded on silica gel, alkylaluminum halide, tris (pentafluorophenol) aluminum, tris (trifluoromethyl butanol) aluminum, triphenylmethyltetra (trifluoromethyl butanol) aluminum salts, tetrafluoroborate, ether tetrafluoroborate, epoxy borane, triethylborane, tris (pentafluorophenyl) borane, tetra (pentafluorophenyl) borate, tri-perfluoroaryl boranes, tetraperfluoroaryl borate, tributyl borate, tetra (3,5-ditrifluoromethyl) phenyl borohydride salt, and tetra (3,5-ditrifluoromethyl) phenyl boron-sodium salts.

The organic solvent is at least one selected from a group consisting of toluene, xylene, n-butane, n-pentane, cyclopentane, methyl cyclopentane, n-hexane, n-heptane, cyclohexane, methylcyclohexane, tetrahydrofuran, dichloromethane, dichloroethane, ethyl ether, and isopropyl ether.

The third purpose of the present disclosure is to provide a usage of the ligand based chromium catalyst, and specifically, it serves as a catalyst in ethylene oligomerization reaction.

The ethylene oligomerization reaction comprises selective trimerization and tetramerization of ethylene.

With respect to the ligand based chromium catalyst according to the present disclosure, selective trimerization and tetramerization of ethylene can be realized by replacing the substituents on N, P, and the ligand so as to produce 1-hexene and 1-octene at the same time. The productivity of 1-hexene and 1-octene ranges from 81% to 87%. 1-hexene and 1-octene can be separated from each other through a rectification method.

In some embodiments, the catalyst of invention, optionally with the co-catalyst disclosed herein, can be used with a homogeneous or heterogeneous carrier. As used herein, the term "carrier" refers to a material that is inert with respect to the composition, the structure, and/or the activities of catalyst of invention. The carrier can be organic or inorganic and liquid or solid. An example of the carrier is an organic solvent of the catalyst of invention.

DETAILED DESCRIPTION OF THE EMBODIMENTS

Figure 1:
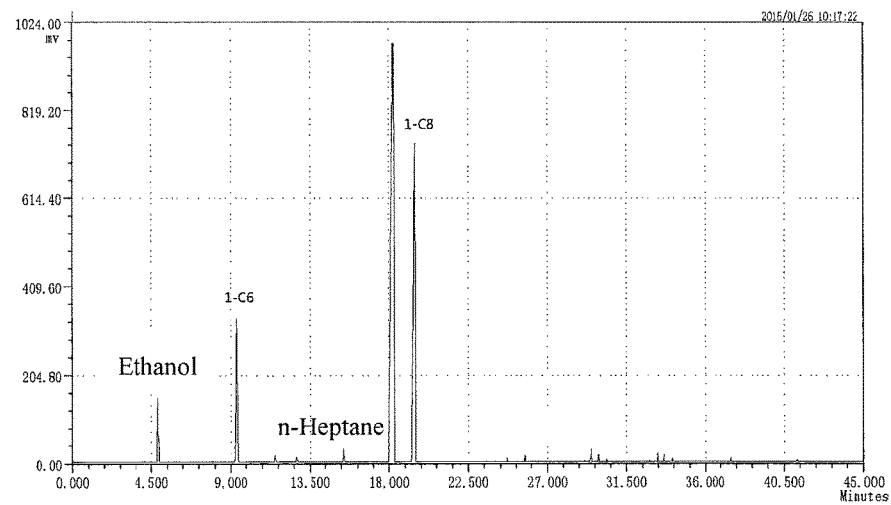
FIG. 1 shows the gas chromatogram of the oligomerization product of Example 5.

The present disclosure will be illustrated in detail hereinafter with reference to the Examples. However, the present disclosure is not limited by the contents of the Examples disclosed herein.

Example 1

1. A ligand is prepared.

O-diphenylphosphino-N-methylaniline (2.91 g, 10 mmol) and toluene (40 mL) are added into a Schlenk bottle (100 mL) in $N_2$ atmosphere. The solution is cooled to $-78°$ C., and an n-hexane solution containing 10 mmol of n-butyl lithium is added into the solution under stirring. The reaction proceeds until a temperature thereof reaches room temperature, and the solution is stirred for another 3 hours. The reaction solution is then cooled to $-78°$ C., and a toluene solution containing 10 mmol of bis (2,4,6-trimethylphenyl)-bromopropyl phosphonium is added into the solution under stirring. The reaction proceeds until the temperature thereof reaches room temperature, and the solution is stirred for another 12 hours.

After completion of the reaction, insoluble substance, i.e., lithium bromide is removed through filtration. The residual solution is separated by a chromatographic column, and is eluted by n-hexane. All of the solution is collected, and all solvent is removed by a rotary evaporator so as to obtain a yellow solid product. A productivity of the product is 45%.

The elemental analysis results are shown as follows. Calculation values: N, 2.33; C, 79.84; H, 7.54. Measured values: N, 2.15; C, 79.89; H, 7.46.

2. A ligand chromium compound is prepared.

The ligand (0.60 g, 1 mmol) prepared in step 1, chromium trichloride(THF)$_3$ (0.37 g, 1 mmol) and THF solvent (50 mL) are added into a Schlenk bottle (100 mL) in $N_2$ atmosphere. The reaction liquid is stirred for 25 hours. The solvent is removed with reduced temperature. Crude product is washed by n-hexane for several times so as to obtain a dark green solid product. A productivity of the product is 91%, and a structure thereof is shown in formula (1) as follows:

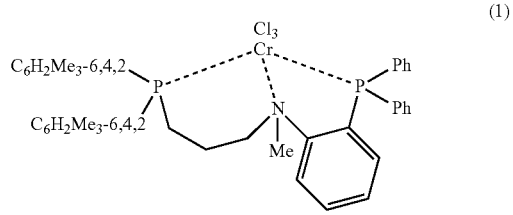

(1)

The elemental analysis results are shown as follows. Calculation values: N, 1.84; C, 63.21; H, 5.97. Measured values: N, 1.75; C, 63.30; H, 5.86.

3. A catalyst formed by the NP-ligand chromium compound as shown in formula (1) and methylaluminoxane (MAO) is used in an ethylene oligomerization reaction, and a method is described as follows.

A high pressure reactor (300 mL) is pre-treated. That is, the reactor is dried by an electric drier and is installed. The reactor is evacuated for 2 hours under a temperature being 50° C. to form a vacuum therein. A fully dried ethylene gas with a certain pressure is pumped into the reactor after $N_2$ replacement for three times, and then a temperature of the reactor drops to room temperature.

Toluene solvent (60 mL) and methylaluminoxane (MAO) (2.5 mL) as co-catalyst are added into the reactor in an ethylene atmosphere. After stirring for 5 minutes, a toluene solution (20 mL) containing 5 μmol of the NP-ligand chromium compound as shown in formula (1) is added into the reactor. A temperature of the reactor is raised to 30° C. under stirring, and reaction proceeds for 30 minutes under ethylene pressure being 3.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%. Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatographic analysis and calculation, and the activity of the catalyst and product compositions are shown in Table 1.

Example 2

A reaction temperature is changed to be 40° C. from 30° C. in Example 1, and other operating conditions are not changed. The reaction results are shown in Table 1.

Example 3

A reaction temperature is changed to be 50° C. from 30° C. in Example 1, and other operating conditions are not changed. The reaction results are shown in Table 1.

Example 4

A reaction temperature is changed to be 60° C. from 30° C. in Example 1, and other operating conditions are not changed. The reaction results are shown in Table 1.

Example 5

A reaction temperature is changed to be 70° C. from 30° C. in Example 1, and other operating conditions are not changed. The reaction results are shown in Table 1, and a gas chromatogram of an oligomerization product thereof is shown in FIG. 1.

Example 6

A reaction pressure is changed to be 3.5 MPa from 3.0 MPa in Example 1, a reaction temperature is changed to be 50° C. from 30° C. in Example 1, and other operating conditions are not changed. The reaction results are shown in Table 1.

Example 7

Figure 2:
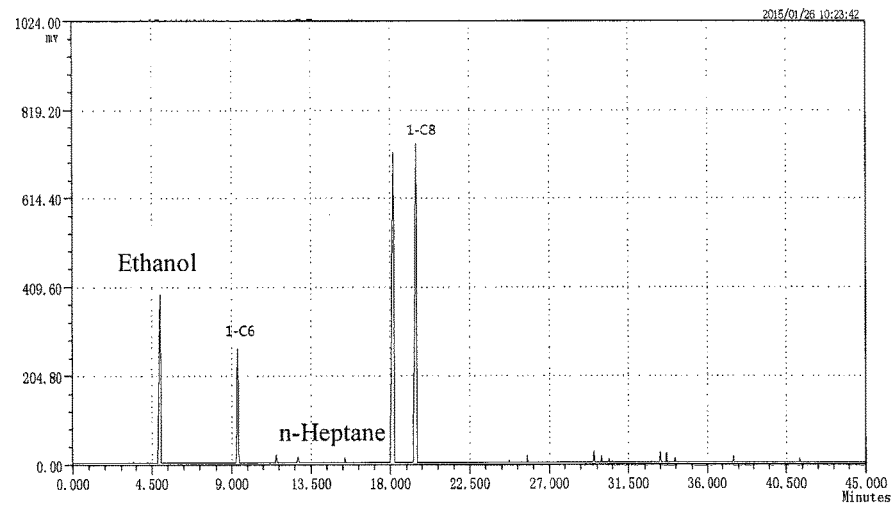
FIG. 2 shows the gas chromatogram of the oligomerization product of Example 7.

A reaction pressure is changed to be 4.0 MPa from 3.0 MPa in Example 1, a reaction temperature is changed to be 50° C. from 30° C. in Example 1, and other operating conditions are not changed. The reaction results are shown in Table 1, and a gas chromatogram of an oligomerization product thereof is shown in FIG. 2.

Example 8

A reaction pressure is changed to be 4.5 MPa from 3.0 MPa in Example 1, a reaction temperature is changed to be 50° C. from 30° C. in Example 1, and other operating conditions are not changed. The reaction results are shown in Table 1.

Example 9

A catalyst formed by the NP-ligand prepared in step 1 of Example 1, chromium compound chromium trichloride $(THF)_3$, and methylaluminoxane (MAO) is used in an ethylene oligomerization reaction, and a method is described as follows.

A high pressure reactor (300 mL) is pre-treated. That is, the reactor is dried by an electric drier and is installed. The reactor is evacuated for 2 hours with a temperature being 50° C. to form a vacuum therein. A fully dried ethylene gas with a certain pressure is pumped into the reactor after $N_2$ replacement for three times, and then a temperature of the reactor drops to room temperature.

A toluene solution (20 mL) containing 20 μmol of NP-ligand prepared in step 1 of Example 1, a toluene suspension (20 mL) containing 20 μmol of chromium trichloride $(THF)_3$, and toluene solvent (20 mL) are added into the reactor in sequence in an ethylene atmosphere. A temperature of the reactor is raised to 50° C., and the mixed solution is stirred for 5 minutes. Methylaluminoxane (MAO) (10 mL) as co-catalyst is then added into the reactor. Reaction proceeds for 30 minutes under stirring with ethylene pressure being 4.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%. Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatographic analysis and calculation, and the activity of the catalyst and product compositions are shown in Table 2.

Example 10

According to the present Example, chromium trichloride $(THF)_3$ in Example 9 is replaced to be chromium dichloride $(THF)_2$, and other operating conditions are not changed. The reaction results are shown in Table 2.

Example 11

According to the present Example, chromium trichloride $(THF)_3$ in Example 9 is replaced to be chromium acetylacetonate, i.e., $Cr(acac)_3$, and other operating conditions are not changed. The reaction results are shown in Table 2.

Example 12

According to the present Example, chromium trichloride $(THF)_3$ in Example 9 is replaced to be chromium tris (2-ethylhexanoate), i.e., $Cr(EH)_3$, and other operating conditions are not changed. The reaction results are shown in Table 2.

Example 13

According to the present Example, chromium trichloride $(THF)_3$ in Example 9 is replaced to be chromium dichloride (tolyl)$(THF)_3$, and other operating conditions are not changed. The reaction results are shown in Table 2.

Example 14

According to the present Example, chromium trichloride $(THF)_3$ in Example 9 is replaced to be chromium dichloride, and other operating conditions are not changed. The reaction results are shown in Table 2.

Example 15

According to the present Example, chromium trichloride $(THF)_3$ in Example 9 is replaced to be chromium trichloride, and other operating conditions are not changed. The reaction results are shown in Table 2.

Example 16

According to the present Example, chromium trichloride (THF)$_3$ in Example 9 is replaced to be CrMe$_2$(:C)$_2$ (:C is a nitrogen heterocyclic carbene, and a molecular formula thereof is C[N(iPr)C(Me)]$_2$), and other operating conditions are not changed. The reaction results are shown in Table 2.

Example 17

According to the present Example, chromium trichloride (THF)$_3$ in Example 9 is replaced to be CrEt$_2$(:C)$_2$ (:C is a nitrogen heterocyclic carbene, and a molecular formula thereof is C[N(iPr)C(Me)]$_2$), and other operating conditions are not changed. The reaction results are shown in Table 2.

Example 18

According to the present Example, chromium trichloride (THF)$_3$ in Example 9 is replaced to be CrPh$_2$(:C)$_2$ (:C is a nitrogen heterocyclic carbene, and a molecular formula thereof is C[N(iPr)C(Me)]$_2$), and other operating conditions are not changed. The reaction results are shown in Table 2.

Example 19

According to the present Example, chromium trichloride (THF)$_3$ in Example 9 is replaced to be CrPh$_3$(THF)$_3$, and other operating conditions are not changed. The reaction results are shown in Table 2.

Example 20

According to the present Example, chromium trichloride (THF)$_3$ in Example 9 is replaced to be Cr(CO)$_6$, and other operating conditions are not changed. The reaction results are shown in Table 2.

Example 21

According to the present Example, chromium trichloride (THF)$_3$ in Example 9 is replaced to be CrMeCl$_2$(THF)$_3$, and other operating conditions are not changed. The reaction results are shown in Table 2.

Example 22

1. A ligand is prepared.

O-(diphenylphosphino)aniline (2.77 g, 10 mmol) and toluene (40 mL) are added into a Schlenk bottle (100 mL) in N$_2$ atmosphere. The solution is cooled to −78° C., and an n-hexane solution containing 10 mmol of n-butyl lithium is added into the solution under stirring. The reaction proceeds until a temperature thereof reaches room temperature, and the solution is stirred for another 3 hours. The reaction solution is then cooled to −78° C., and a toluene solution containing 10 mmol of bis (2,4,6-trimethylphenyl)-bromopropyl phosphonium is added into the solution under stirring. The reaction proceeds until the temperature thereof reaches room temperature, and the solution is stirred for another 12 hours.

After completion of the reaction, insoluble substance, i.e., lithium bromide is removed through filtration. The residual solution is separated by a chromatographic column, and is eluted by n-hexane. All of the solution is collected, and all solvent is removed by a rotary evaporator so as to obtain a light yellow solid product. A productivity of the product is 33%.

The elemental analysis results are shown as follows. Calculation values: N, 2.38; C, 79.70; H, 7.37. Measured values: N, 2.35; C, 79.78; H, 7.36.

2. A ligand chromium compound is prepared.

The ligand (0.59 g, 1 mmol) prepared in step 1, chromium trichloride(THF)$_3$ (0.37 g, 1 mmol) and THF solvent (50 mL) are added into a Schlenk bottle (100 mL) in N$_2$ atmosphere. The reaction liquid is stirred for 25 hours. The solvent is removed with reduced temperature. Crude product is washed by n-hexane for several times so as to obtain a dark green solid product. A productivity of the product is 93%, and a structure thereof is shown in formula (2) as follows:

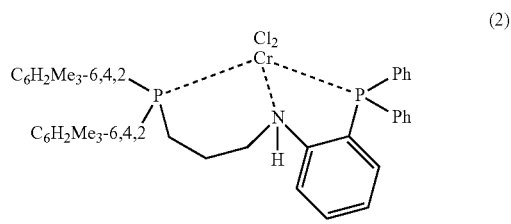

(2)

The elemental analysis results are shown as follows. Calculation values: N, 1.88; C, 62.78; H, 5.81. Measured values: N, 1.92; C, 62.89; H, 5.76.

3. A catalyst formed by the NP-ligand chromium compound as shown in formula (2) and methylaluminoxane (MAO) is used in an ethylene oligomerization reaction, and a method is described as follows.

A high pressure reactor (300 mL) is pre-treated. That is, the reactor is dried by an electric drier and is installed. The reactor is evacuated for 2 hours under a temperature being 50° C. to form a vacuum therein. A fully dried ethylene gas with a certain pressure is pumped into the reactor after N$_2$ replacement for three times, and then a temperature of the reactor drops to room temperature.

Toluene solvent (60 mL) and methylaluminoxane (MAO) (2.5 mL) as co-catalyst are added into the reactor in an ethylene atmosphere. After stirring for 5 minutes, a toluene solution (20 mL) containing 5 μmol of the NP-ligand chromium compound as shown in formula (2) is added into the reactor. A temperature of the reactor is raised to 50° C. under stirring, and reaction proceeds for 30 minutes under ethylene pressure being 4.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%. Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatography analysis and calculation, and the activity of the catalyst and product compositions are shown in Table 3.

Example 23

1. A ligand is prepared.

O-diphenylphosphino-N-methylaniline (2.91 g, 10 mmol) and toluene (40 mL) are added into a Schlenk bottle (100 mL) in $N_2$ atmosphere. The solution is cooled to −78° C., and an n-hexane solution containing 10 mmol of n-butyl lithium is added into the solution under stirring. The reaction proceeds until a temperature thereof reaches room temperature, and the solution is stirred for another 3 hours. The reaction solution is then cooled to −78° C., and a toluene solution containing 10 mmol of diphenyl-bromopropyl phosphonium is added into the solution under stirring. The reaction proceeds until the temperature thereof reaches room temperature, and the solution is stirred for another 12 hours.

After completion of the reaction, insoluble substance, i.e., lithium bromide is removed through filtration. The residual solution is separated by a chromatographic column, and is eluted by n-hexane. All of the solution is collected, and all solvent is removed by a rotary evaporator so as to obtain a light yellow solid product. A productivity of the product is 62%.

The elemental analysis results are shown as follows. Calculation values: N, 2.71; C, 78.90; H, 6.43. Measured values: N, 2.63; C, 78.89; H, 6.34.

2. A ligand chromium compound is prepared.

The ligand (0.52 g, 1 mmol) prepared in step 1, chromium trichloride(THF)$_3$ (0.37 g, 1 mmol) and THF solvent (50 mL) are added into a Schlenk bottle (100 mL) in $N_2$ atmosphere. The reaction liquid is stirred for 25 hours. The solvent is removed with reduced temperature. Crude product is washed by n-hexane for several times so as to obtain a dark green solid product. A productivity of the product is 90%, and a structure thereof is shown in formula (3) as follows:

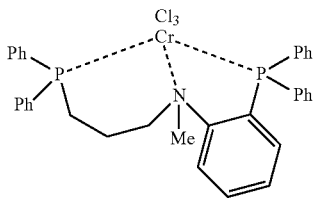

(3)

The elemental analysis results are shown as follows. Calculation values: N, 2.07; C, 60.41; H, 4.92. Measured values: N, 2.05; C, 60.59; H, 5.01.

3. A catalyst formed by the NP-ligand chromium compound as shown in formula (3) and methylaluminoxane (MAO) is used in an ethylene oligomerization reaction, and a method is described as follows.

A high pressure reactor (300 mL) is pre-treated. That is, the reactor is dried by an electric drier and is installed. The reactor is evacuated for 2 hours under a temperature being 50° C. to form a vacuum therein. A fully dried ethylene gas with a certain pressure is pumped into the reactor after $N_2$ replacement for three times, and then a temperature of the reactor drops to room temperature.

Toluene solvent (60 mL) and methylaluminoxane (MAO) (2.5 mL) as co-catalyst are added into the reactor in an ethylene atmosphere. After stirring for 5 minutes, a toluene solution (20 mL) containing 5 μmol of the NP-ligand chromium compound as shown in formula (3) is added into the reactor. A temperature of the reactor is raised to 50° C. under stirring, and reaction proceeds for 30 minutes with ethylene pressure being 4.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%. Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatographic analysis and calculation, and the activity of the catalyst and product compositions are shown in Table 3.

Example 24

1. A ligand is prepared.

O-(diphenylphosphino) aniline (2.77 g, 10 mmol) and toluene (40 mL) are added into a Schlenk bottle (100 mL) in $N_2$ atmosphere. The solution is cooled to −78° C., and an n-hexane solution containing 10 mmol of n-butyl lithium is added into the solution under stirring. The reaction proceeds until a temperature thereof reaches room temperature, and the solution is stirred for another 3 hours. The reaction solution is then cooled to −78° C., and a toluene solution containing 10 mmol of diphenyl-bromopropyl phosphonium is added into the solution under stirring. The reaction proceeds until the temperature thereof reaches room temperature, and the solution is stirred for another 12 hours.

After completion of the reaction, insoluble substance, i.e., lithium bromide is removed through filtration. The residual solution is separated by a chromatographic column, and is eluted by n-hexane. All of the solution is collected, and all solvent is removed by a rotary evaporator so as to obtain a light yellow solid product. A productivity of the product is 43%.

The elemental analysis results are shown as follows. Calculation values: N, 2.78; C, 78.71; H, 6.21. Measured values: N, 2.73; C, 78.68; H, 6.16.

2. A ligand chromium compound is prepared.

The ligand (0.51 g, 1 mmol) prepared in step 1, chromium trichloride(THF)$_3$ (0.37 g, 1 mmol) and THF solvent (50 mL) are added into a Schlenk bottle (100 mL) in $N_2$ atmosphere. The reaction liquid is stirred for 25 hours. The solvent is removed with reduced temperature. Crude product is washed by n-hexane for several times so as to obtain a dark green solid product. A productivity of the product is 88%, and a structure thereof is shown in formula (4) as follows:

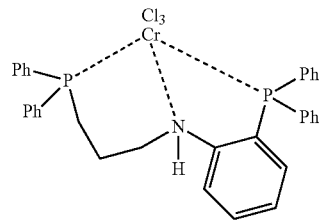

(4)

The elemental analysis results are shown as follows. Calculation values: N, 2.12; C, 59.88; H, 4.72. Measured values: N, 2.15; C, 60.02; H, 4.66.

3. A catalyst formed by the NP-ligand chromium compound as shown in formula (4) and methylaluminoxane (MAO) is used in an ethylene oligomerization reaction, and a method is described as follows.

A high pressure reactor (300 mL) is pre-treated. That is, the reactor is dried by an electric drier and is installed. The reactor is evacuated for 2 hours under a temperature being 50° C. to form a vacuum therein. A fully dried ethylene gas with a certain pressure is pumped into the reactor after $N_2$ replacement for three times, and then a temperature of the reactor drops to room temperature.

Toluene solvent (60 mL) and methylaluminoxane (MAO) (2.5 mL) as co-catalyst are added into the reactor in an ethylene atmosphere. After stirring for 5 minutes, a toluene solution (20 mL) containing 5 μmol of the NP-ligand chromium compound as shown in formula (4) is added into the reactor. A temperature of the reactor is raised to 50° C. under stirring, and reaction proceeds for 30 minutes under ethylene pressure being 4.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%. Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatographic analysis and calculation, and the activity of the catalyst and product compositions are shown in Table 3.

Example 25

1. A ligand is prepared.
O-diphenylphosphino-N-methylaniline (2.91 g, 10 mmol) and toluene (40 mL) are added into a Schlenk bottle (100 mL) in $N_2$ atmosphere. The solution is cooled to −78° C., and an n-hexane solution containing 10 mmol of n-butyl lithium is added into the solution under stirring. The reaction proceeds until a temperature thereof reaches room temperature, and the solution is stirred for another 3 hours. The reaction solution is then cooled to −78° C., and a toluene solution containing 10 mmol of dicyclohexyl-bromopropyl phosphonium is added into the solution under stirring. The reaction proceeds until the temperature thereof reaches room temperature, and the solution is stirred for another 12 hours.

After completion of the reaction, insoluble substance, i.e., lithium bromide is removed through filtration. The residual solution is separated by a chromatographic column, and is eluted by n-hexane. All of the solution is collected, and all solvent is removed by a rotary evaporator so as to obtain a light yellow solid product. A productivity of the product is 51%.

The elemental analysis results are shown as follows. Calculation values: N, 2.64; C, 77.10; H, 8.56. Measured values: N, 2.55; C, 77.15; H, 8.49.

2. A ligand chromium compound is prepared.
The ligand (0.53 g, 1 mmol) prepared in step 1, chromium trichloride(THF)₃ (0.37 g, 1 mmol) and THF solvent (50 mL) are added into a Schlenk bottle (100 mL) in $N_2$ atmosphere. The reaction liquid is stirred for 25 hours. The solvent is removed with reduced temperature. Crude product is washed by n-hexane for several times so as to obtain a dark green solid product. A productivity of the product is 90%, and a structure thereof is shown in formula (5) as follows:

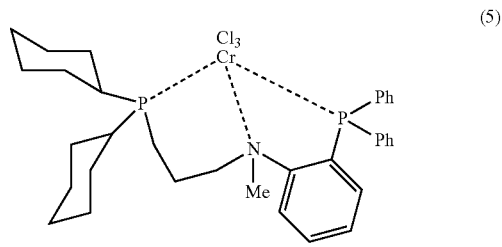

(5)

The elemental analysis results are shown as follows. Calculation values: N, 2.04; C, 59.35; H, 6.59. Measured values: N, 2.01; C, 58.89; H, 6.47.

3. A catalyst formed by the NP-ligand chromium compound as shown in formula (5) and methylaluminoxane (MAO) is used in an ethylene oligomerization reaction, and a method is described as follows.

A high pressure reactor (300 mL) is pre-treated. That is, the reactor is dried by an electric drier and is installed. The reactor is evacuated for 2 hours under a temperature being 50° C. to form a vacuum therein. A fully dried ethylene gas with a certain pressure is pumped into the reactor after $N_2$ replacement for three times, and then a temperature of the reactor drops to room temperature.

Toluene solvent (60 mL) and methylaluminoxane (MAO) (2.5 mL) as co-catalyst are added into the reactor in an ethylene atmosphere. After stirring for 5 minutes, a toluene solution (20 mL) containing 5 μmol of the NP-ligand chromium compound as shown in formula (5) is added into the reactor. A temperature of the reactor is raised to 50° C. under stirring, and reaction proceeds for 30 minutes under ethylene pressure being 4.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%. Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatographic analysis and calculation, and the activity of the catalyst and product compositions are shown in Table 3.

Example 26

1. A ligand is prepared.
O-(diphenylphosphino) aniline (2.77 g, 10 mmol) and toluene (40 mL) are added into a Schlenk bottle (100 mL) in $N_2$ atmosphere. The solution is cooled to −78° C., and an n-hexane solution containing 10 mmol of n-butyl lithium is added into the solution under stirring. The reaction proceeds until a temperature thereof reaches room temperature, and the solution is stirred for another 3 hours. The reaction solution is then cooled to −78° C., and a toluene solution containing 10 mmol of dicyclohexyl-bromopropyl phosphonuim is added into the solution under stirring. The reaction proceeds until the temperature thereof reaches room temperature, and the solution is stirred for another 12 hours.

After completion of the reaction, insoluble substance, i.e., lithium bromide is removed through filtration. The residual solution is separated by a chromatographic column, and is eluted by n-hexane. All of the solution is collected, and all solvent is removed by a rotary evaporator so as to obtain a light yellow solid product. A productivity of the product is 22%.

The elemental analysis results are shown as follows. Calculation values: N, 2.71; C, 76.71; H, 8.50. Measured values: N, 2.65; C, 76.70; H, 8.46.

2. A ligand chromium compound is prepared.

The ligand (0.51 g, 1 mmol) prepared in step 1, chromium trichloride(THF)$_3$ (0.37 g, 1 mmol) and THF solvent (50 mL) are added into a Schlenk bottle (100 mL) in N$_2$ atmosphere. The reaction liquid is stirred for 25 hours. The solvent is removed with reduced temperature. Crude product is washed by n-hexane for several times so as to obtain a dark green solid product. A productivity of the product is 85%, and a structure thereof is shown in formula (6) as follows:

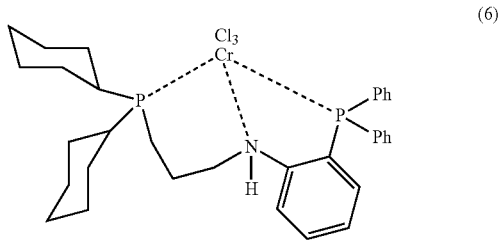

(6)

The elemental analysis results are shown as follows. Calculation values: N, 2.08; C, 58.72; H, 6.57. Measured values: N, 2.15; C, 68.84; H, 6.43.

3. A catalyst formed by the NP-ligand chromium compound as shown in formula (6) and methylaluminoxane (MAO) is used in an ethylene oligomerization reaction, and a method is described as follows.

A high pressure reactor (300 mL) is pre-treated. That is, the reactor is dried by an electric drier and is installed. The reactor is evacuated for 2 hours with a temperature being 50° C. to form a vacuum therein. A fully dried ethylene gas with a certain pressure is pumped into the reactor after N$_2$ replacement for three times, and then a temperature of the reactor drops to room temperature.

Toluene solvent (60 mL) and methylaluminoxane (MAO) (2.5 mL) as co-catalyst are added into the reactor in an ethylene atmosphere. After stirring for 5 minutes, a toluene solution (20 mL) containing 5 μmol of the NP-ligand chromium compound as shown in formula (6) is added into the reactor. A temperature of the reactor is raised to 50° C. under stirring, and reaction proceeds for 30 minutes under ethylene pressure being 4.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%. Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatographic analysis and calculation, and the activity of the catalyst and product compositions are shown in Table 3.

Example 27

In the present Example, a ligand and a ligand chromium compound can be prepared according to the method of Example 1.

A catalyst formed by an NP-ligand chromium compound as shown in formula (7) and methylaluminoxane (MAO) is used in an ethylene oligomerization reaction, and a method is described as follows.

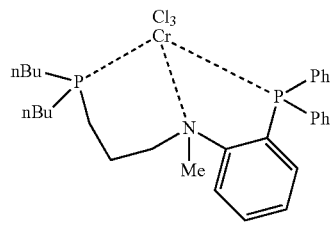

(7)

A high pressure reactor (300 mL) is pre-treated. That is, the reactor is dried by an electric drier and is installed. The reactor is evacuated for 2 hours under a temperature being 50° C. to form a vacuum therein. A fully dried ethylene gas with a certain pressure is pumped into the reactor after N2 replacement for three times, and then a temperature of the reactor drops to room temperature.

Toluene solvent (60 mL) and methylaluminoxane (MAO) (2.5 mL) as co-catalyst are added into the reactor in an ethylene atmosphere. After stirring for 5 minutes, a toluene solution (20 mL) containing 5 μmol of the NP-ligand chromium compound as shown in formula (7) is added into the reactor. A temperature of the reactor is raised to 50° C. under stirring, and reaction proceeds for 30 minutes under ethylene pressure being 4.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%. Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatographic analysis and calculation, and the activity of the catalyst and product compositions are shown in Table 3.

Example 28

In the present Example, a ligand and a ligand chromium compound can be prepared according to the method of Example 1.

A catalyst formed by an NP-ligand chromium compound as shown in formula (8) and methylaluminoxane (MAO) is used in an ethylene oligomerization reaction, and a method is described as follows.

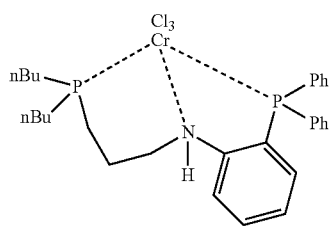

(8)

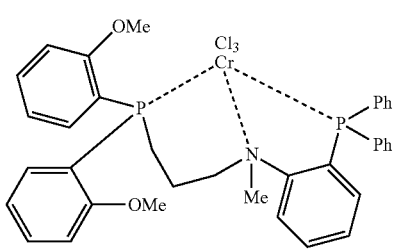

(9)

A high pressure reactor (300 mL) is pre-treated. That is, the reactor is dried by an electric drier and is installed. The reactor is evacuated for 2 hours under a temperature being 50° C. to form a vacuum therein. A fully dried ethylene gas with a certain pressure is pumped into the reactor after $N_2$ replacement for three times, and then a temperature of the reactor drops to room temperature.

Toluene solvent (60 mL) and methylaluminoxane (MAO) (2.5 mL) as co-catalyst are added into the reactor in an ethylene atmosphere. After stirring for 5 minutes, a toluene solution (20 mL) containing 5 μmol of the NP-ligand chromium compound as shown in formula (8) is added into the reactor. A temperature of the reactor is raised to 50° C. under stirring, and reaction proceeds for 30 minutes under ethylene pressure being 4.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%. Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatographic analysis and calculation, and the activity of the catalyst and product compositions are shown in Table 3.

Example 29

In the present Example, a ligand and a ligand chromium compound can be prepared according to the method of Example 1.

A catalyst formed by an NP-ligand chromium compound as shown in formula (9) and methylaluminoxane (MAO) is used in an ethylene oligomerization reaction, and a method is described as follows.

A high pressure reactor (300 mL) is pre-treated. That is, the reactor is dried by an electric drier and is installed. The reactor is evacuated for 2 hours under a temperature being 50° C. to form a vacuum therein. A fully dried ethylene gas with a certain pressure is pumped into the reactor after $N_2$ replacement for three times, and then a temperature of the reactor drops to room temperature.

Toluene solvent (60 mL) and methylaluminoxane (MAO) (2.5 mL) as co-catalyst are added into the reactor in an ethylene atmosphere. After stirring for 5 minutes, a toluene solution (20 mL) containing 5 μmol of the NP-ligand chromium compound as shown in formula (9) is added into the reactor. A temperature of the reactor is raised to 50° C. under stirring, and reaction proceeds for 30 minutes under ethylene pressure being 4.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%. Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatographic analysis and calculation, and the activity of the catalyst and product compositions are shown in Table 3.

Example 30

In the present Example, a ligand and a ligand chromium compound can be prepared according to the method of Example 1.

A catalyst formed by an NP-ligand chromium compound as shown in formula (10) and methylaluminoxane (MAO) is used in an ethylene oligomerization reaction, and a method is described as follows.

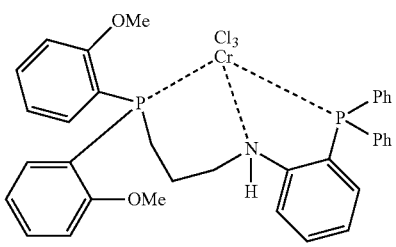

(10)

A high pressure reactor (300 mL) is pre-treated. That is, the reactor is dried by an electric drier and is installed. The reactor is evacuated for 2 hours under a temperature being 50° C. to form a vacuum therein. A fully dried ethylene gas with a certain pressure is pumped into the reactor after N₂ replacement for three times, and then a temperature of the reactor drops to room temperature.

Toluene solvent (60 mL) and methylaluminoxane (MAO) (2.5 mL) as co-catalyst are added into the reactor in an ethylene atmosphere. After stirring for 5 minutes, a toluene solution (20 mL) containing 5 µmol of the NP-ligand chromium compound as shown in formula (10) is added into the reactor. A temperature of the reactor is raised to 50° C. under stirring, and reaction proceeds for 30 minutes under ethylene pressure being 4.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%. Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatographic analysis and calculation, and the activity of the catalyst and product compositions are shown in Table 3.

Example 31

1. A ligand is prepared.

O-(diphenylphosphino)bromobenzene (20 mmol), N,N-dimethyl methylamine (50 mmol), N,N-dimethyl methanamide solvent (40 mL), and CuI catalyst (0.5 g) are added into a Schlenk bottle (100 mL) in N₂ atmosphere. The mixed liquid is heated to 80° C. and kept for 12 hours at such a temperature.

After completion of the reaction, the liquid is cooled to room temperature. Insoluble substances are removed through filtration. The residual solution is separated by a chromatographic column, and is eluted by n-hexane. All solution is collected, and all solvent and volatile compositions are removed through a vacuum decompression method so as to obtain a white solid product. A productivity of the product is 31%.

The elemental analysis results are shown as follows. Calculation values: N, 8.38; C, 75.43; H, 6.93. Measured values: N, 8.35; C, 75.50; H, 6.95.

2. A ligand chromium compound is prepared.

The ligand (0.33 g, 1 mmol) prepared in step 1, chromium trichloride(THF)₃ (0.37 g, 1 mmol) and THF solvent (50 mL) are added into a Schlenk bottle (100 mL) in N₂ atmosphere. The reaction liquid is stirred for 25 hours. The solvent is removed with reduced temperature. Crude product is washed by n-hexane so as to obtain a dark green solid product. A productivity of the product is 80%, and a structure thereof is shown in formula (11) as follows:

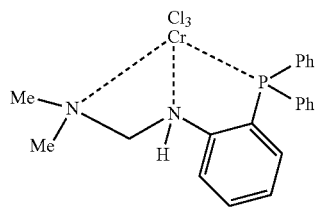

(11)

The elemental analysis results are shown as follows. Calculation values: N, 5.69; C, 51.19; H, 4.70. Measured values: N, 5.62; C, 51.41; H, 4.66.

3. A catalyst formed by the NP-ligand chromium compound as shown in formula (11) and methylaluminoxane (MAO) is used in an ethylene oligomerization reaction, and a method is described as follows.

A high pressure reactor (300 mL) is pre-treated. That is, the reactor is dried by an electric drier and is installed. The reactor is evacuated for 2 hours under a temperature being 50° C. to form a vacuum therein. A fully dried ethylene gas with a certain pressure is pumped into the reactor after N₂ replacement for three times, and then a temperature of the reactor drops to room temperature.

Toluene solvent (60 mL) and methylaluminoxane (MAO) (2.5 mL) as co-catalyst are added into the reactor in an ethylene atmosphere. After stirring for 5 minutes, a toluene solution (20 mL) containing 5 µmol of the NP-ligand chromium compound as shown in formula (11) is added into the reactor. A temperature of the reactor is raised to 50° C. under stirring, and reaction proceeds for 30 minutes under ethylene pressure being 4.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%.

Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatographic analysis and calculation, and the activity of the catalyst and product compositions are shown in Table 3.

Example 32

1. A ligand is prepared.

O-(diphenylphosphino)bromobenzene (20 mmol), N,N-dimethyl ethylamine (50 mmol), N,N-dimethyl methanamide solvent (40 mL), and CuI catalyst (0.5 g) are added into a Schlenk bottle (100 mL) in N₂ atmosphere. The mixed liquid is heated to 80° C. and kept for 12 hours at such a temperature.

After completion of the reaction, the liquid is cooled to room temperature. Insoluble substances are removed through filtration. The residual solution is separated by a chromatographic column, and is eluted by n-hexane. All solution is collected, and all solvent and volatile compositions are removed through a vacuum decompression method so as to obtain a white solid product. A productivity of the product is 37%.

The elemental analysis results are shown as follows. Calculation values: N, 8.04; C, 75.84; H, 7.23. Measured values: N, 8.05; C, 75.69; H, 7.27.

2. A ligand chromium compound is prepared.

The ligand (0.35 g, 1 mmol) prepared in step 1, chromium trichloride(THF)₃ (0.37 g, 1 mmol) and THF solvent (50 mL) are added into a Schlenk bottle (100 mL) in N₂ atmosphere. The reaction liquid is stirred for 25 hours. The solvent is removed with reduced temperature. Crude product is washed by n-hexane so as to obtain a dark green solid product. A productivity of the product is 91%, and a structure thereof is shown in formula (12) as follows:

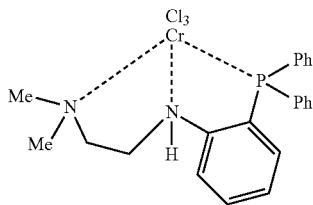

(12)

The elemental analysis results are shown as follows. Calculation values: N, 5.53; C, 52.14; H, 4.97. Measured values: N, 5.65; C, 52.12; H, 4.76.

3. A catalyst formed by the NP-ligand chromium compound as shown in formula (12) and methylaluminoxane (MAO) is used in an ethylene oligomerization reaction, and a method is described as follows.

A high pressure reactor (300 mL) is pre-treated. That is, the reactor is dried by an electric drier and is installed. The reactor is evacuated for 2 hours with a temperature being 50° C. to form a vacuum therein. A fully dried ethylene gas with a certain pressure is pumped into the reactor after $N_2$ replacement for three times, and then a temperature of the reactor drops to room temperature.

Toluene solvent (60 mL) and methylaluminoxane (MAO) (2.5 mL) as co-catalyst are added into the reactor in an ethylene atmosphere. After stirring for 5 minutes, a toluene solution (20 mL) containing 5 μmol of the NP-ligand chromium compound as shown in formula (12) is added into the reactor. A temperature of the reactor is raised to 50° C. under stirring, and reaction proceeds for 30 minutes under ethylene pressure being 4.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%. Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatographic analysis and calculation, and the activity of the catalyst and product compositions are shown in Table 3.

Example 33

1. A ligand is prepared.

O-(diphenylphosphino)bromobenzene (20 mmol), diphenylphosphino methylamine (20 mmol), triethylamine (50 mmol), N,N-dimethyl methanamide solvent (40 mL), and CuI catalyst (0.5 g) are added into a Schlenk bottle (100 mL) in $N_2$ atmosphere. The mixed liquid is heated to 80° C. and kept for 12 hours at such a temperature.

After completion of the reaction, the liquid is cooled to room temperature. Insoluble substances are removed through filtration. The residual solution is separated by a chromatographic column, and is eluted by n-hexane. All solution is collected, and all solvent and volatile compositions are removed through a vacuum decompression method. Solid product obtained therein is recrystallized so as to obtain a light yellow crystalline product. A productivity of the product is 28%.

The elemental analysis results are shown as follows. Calculation values: N, 2.95; C, 78.30; H, 5.72. Measured values: N, 2.87; C, 78.41; H, 5.76.

2. A ligand chromium compound is prepared.

The ligand (0.48 g, 1 mmol) prepared in step 1, chromium trichloride(THF)$_3$ (0.37 g, 1 mmol) and THF solvent (50 mL) are added into a Schlenk bottle (100 mL) in $N_2$ atmosphere. The reaction liquid is stirred for 25 hours. The solvent is removed with reduced temperature. Crude product is washed by n-hexane so as to obtain a dark green solid product. A productivity of the product is 90%, and a structure thereof is shown in formula (13) as follows:

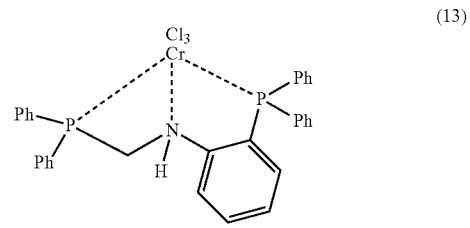

(13)

The elemental analysis results are shown as follows. Calculation values: N, 2.21; C, 58.74; H, 4.29. Measured values: N, 2.15; C, 58.89; H, 4.26.

3. A catalyst formed by the NP-ligand chromium compound as shown in formula (13) and methylaluminoxane (MAO) is used in an ethylene oligomerization reaction, and a method is described as follows.

A high pressure reactor (300 mL) is pre-treated. That is, the reactor is dried by an electric drier and is installed. The reactor is evacuated for 2 hours under a temperature being 50° C. to form a vacuum therein. A fully dried ethylene gas with a certain pressure is pumped into the reactor after $N_2$ replacement for three times, and then a temperature of the reactor drops to room temperature.

Toluene solvent (60 mL) and methylaluminoxane (MAO) (2.5 mL) as co-catalyst are added into the reactor in an ethylene atmosphere. After stirring for 5 minutes, a toluene solution (20 mL) containing 5 μmol of the NP-ligand chromium compound as shown in formula (1) is added into the reactor. A temperature of the reactor is raised to 50° C. under stirring, and reaction proceeds for 30 minutes under ethylene pressure being 4.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%. Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatographic analysis and calculation, and the activity of the catalyst and product compositions are shown in Table 3.

Example 34

1. A ligand is prepared.

O-(diphenylphosphino)bromobenzene (20 mmol), diphenylphosphino ethylamine (20 mmol), triethylamine (50 mmol), N,N-dimethyl methanamide solvent (40 mL), and CuI catalyst (0.5 g) are added into a Schlenk bottle (100 mL) in $N_2$ atmosphere. The mixed liquid is heated to 80° C. and kept for 12 hours at such a temperature.

After completion of the reaction, the liquid is cooled to room temperature. Insoluble substances are removed through filtration. The residual solution is separated by a chromatographic column, and is eluted by n-hexane. All solution is collected, and all solvent and volatile compositions are removed through a vacuum decompression method so as to obtain a white solid product. A productivity of the product is 46%.

The elemental analysis results are shown as follows. Calculation values: N, 2.86; C, 78.51; H, 5.97. Measured values: N, 2.89; C, 78.49; H, 5.96.

2. A ligand chromium compound is prepared.

The ligand (0.49 g, 1 mmol) prepared in step 1, chromium trichloride(THF)$_3$ (0.37 g, 1 mmol) and THF solvent (50 mL) are added into a Schlenk bottle (100 mL) in $N_2$ atmosphere. The reaction liquid is stirred for 25 hours. The solvent is removed with reduced temperature. Crude product is washed by n-hexane for several times so as to obtain a dark green solid product. A productivity of the product is 91%, and a structure thereof is shown in formula (14) as follows:

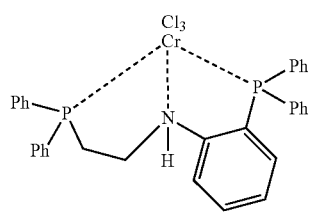

(14)

The elemental analysis results are shown as follows. Calculation values: N, 2.16; C, 59.32; H, 4.51. Measured values: N, 2.13; C, 59.29; H, 4.47.

3. A catalyst formed by the NP-ligand chromium compound as shown in formula (14) and methylaluminoxane (MAO) is used in an ethylene oligomerization reaction, and a method is described as follows.

A high pressure reactor (300 mL) is pre-treated. That is, the reactor is dried by an electric drier and is installed. The reactor is evacuated for 2 hours under a temperature being 50° C. to form a vacuum therein. A fully dried ethylene gas with a certain pressure is pumped into the reactor after $N_2$ replacement for three times, and then a temperature of the reactor drops to room temperature.

Toluene solvent (60 mL) and methylaluminoxane (MAO) (2.5 mL) as co-catalyst are added into the reactor in an ethylene atmosphere. After stirring for 5 minutes, a toluene solution (20 mL) containing 5 μmol of the NP-ligand chromium compound as shown in formula (14) is added into the reactor. A temperature of the reactor is raised to 50° C. under stirring, and reaction proceeds for 30 minutes under ethylene pressure being 4.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%. Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatographic analysis and calculation, and the activity of the catalyst and product compositions are shown in Table 3.

Reference Example 1

1. A ligand is prepared.

N-2,6-diisopropyl phenyl-2-phenyl-2-chloro-imine (29.98 g, 100 mmol), o-(diphenyl phosphino) aniline (27.73 g, 100 mmol), and toluene (400 ml) are added into a Schlenk bottle (100 mL) in $N_2$ atmosphere. The mixed liquid is heated to 120° C. and refluxed for 20 hours so as to obtain a hydrochloride of the ligand.

The hydrochloride is dissolved in ethanol (300 ml, 95%), and is dropwise added to aqueous ammonia (300 ml, 25%) for neutralization. Solid product obtained therein is collected after filtration, is dried in vacuum for 4 hours, and is recrystallized in toluene so as to obtain a white crystalline product. A productivity of the product is 85%.

The elemental analysis results are shown as follows. Calculation values: N, 5.18; C, 82.19; H, 6.71. Measured values: N, 5.06; C, 81.88; H, 6.67.

2. A ligand chromium compound is prepared.

The ligand (0.54 g, 1 mmol) prepared in step 1, chromium trichloride(THF)$_3$ (0.37 g, 1 mmol) and THF solvent (50 mL) are added into a Schlenk bottle (100 mL) in $N_2$ atmosphere. The reaction liquid turns to dark green. The reaction liquid is stirred for 25 hours, and then solvent is removed in vacuum. Crude product is washed by n-hexane for several times so as to obtain a dark green solid product. A productivity of the product is 92.9%, and a structure thereof is shown in formula (15) as follows:

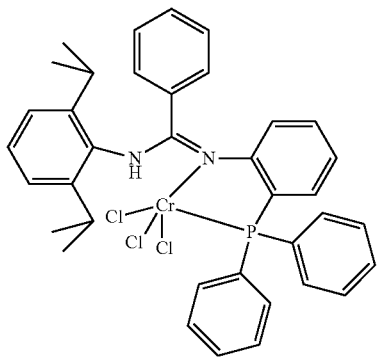

(15)

The elemental analysis results are shown as follows. Calculation values: N, 4.01; C, 63.57; H, 5.19. Measured values: N, 3.91; C, 62.79; H, 5.38.

3. A catalyst formed by the NP-ligand chromium compound as shown in formula (15) and methylaluminoxane (MAO) is used in an ethylene oligomerization reaction, and a method is described as follows.

A high pressure reactor (300 mL) is pre-treated. That is, the reactor is dried by an electric drier and is installed. The reactor is evacuated for 2 hours under a temperature being 50° C. to form a vacuum therein. A fully dried ethylene gas with a certain pressure is pumped into the reactor after $N_2$ replacement for three times, and then a temperature of the reactor drops to room temperature.

Toluene solvent (60 mL) and methylaluminoxane (MAO) (2.5 mL) as co-catalyst are added into the reactor in an ethylene atmosphere. After stirring for 5 minutes, a toluene solution (20 mL) containing 5 μmol of the NP-ligand chromium compound as shown in formula (15) is added into the reactor. A temperature of the reactor is raised to 50° C. under stirring, and reaction proceeds for 30 minutes under ethylene pressure being 4.0 MPa. The reaction goes on until a predetermined time, the stirring stops, a supply of ethylene gas stops, and the temperature of the reactor is reduced to about 5° C. A pressure of the reactor is reduced slowly, and a product after reaction is poured to an ethanol solution acidified with hydrochloric acid with a concentration being 10%. Organic products are separated by adding 100 mL of water. Liquid products are dried by anhydrous sodium sulfate, and are qualitatively and quantitatively analyzed through GC-FID methods. Solid products are collected after filtration, and are dried in vacuum at 50° C. until a weight thereof reaches a constant weight, and the mass percentage content is calculated separately.

An activity of the catalyst can be obtained through gas chromatographic analysis and calculation, and the activity of the catalyst and product compositions are shown in Table 3.

TABLE 1

Activities of the catalysts and product compositions of Examples 1-8

| Examples | Activity ($10^6$ g/ (mol Cr · h)) | $C_6$# (wt %) | 1-$C_6$ in $C_6$ (%) | $C_8$# (wt %) | 1-$C_8$ in $C_8$ (%) | $C_{10+}$# (wt %) | PE* (wt %) |
|---|---|---|---|---|---|---|---|
| 1 | 1.32 | 26.0 | 87.0 | 57.5 | 96.4 | 16.5 | 3.4 |
| 2 | 7.92 | 38.5 | 85.5 | 51.6 | 96.9 | 9.9 | 1.9 |
| 3 | 8.42 | 36.2 | 75.4 | 54.2 | 97.3 | 9.6 | 2.5 |
| 4 | 7.32 | 37.3 | 92.5 | 57.5 | 97.6 | 7.2 | 2.1 |
| 5 | 7.48 | 21.5 | 84.7 | 69.0 | 98.3 | 9.5 | 2.5 |
| 6 | 8.42 | 24.3 | 95.1 | 68.2 | 98.6 | 7.5 | 3.0 |
| 7 | 9.52 | 23.2 | 84.5 | 70.1 | 97.3 | 6.7 | 4.1 |
| 8 | 6.43 | 20.8 | 73.5 | 68.9 | 98.1 | 10.3 | 2.1 |

According to Table 1, data in columns with sign "#" represent mass percentage content of each composition in the oligomerization products, and *PE represents mass percentage content thereof in total mass.

TABLE 2

Activities of the catalysts and product compositions of Examples 9-21

| Examples | Activity ($10^6$ g/ (mol Cr · h)) | $C_6$# (wt %) | 1-$C_6$ in $C_6$ (%) | $C_8$# (wt %) | 1-$C_8$ in $C_8$ (%) | $C_{10+}$# (wt %) | PE* (wt %) |
|---|---|---|---|---|---|---|---|
| 9 | 6.24 | 25.1 | 75.9 | 71.1 | 98.5 | 3.8 | 1.4 |
| 10 | 0.42 | 27.1 | 64.2 | 57.6 | 97.1 | 15.3 | 1.0 |
| 11 | 1.32 | 24.7 | 69.5 | 61.5 | 97.9 | 13.8 | 2.6 |
| 12 | 3.03 | 34.3 | 82.5 | 58.5 | 98.1 | 7.2 | 1.8 |
| 13 | 0.52 | 20.6 | 74.5 | 67.0 | 99.2 | 11.8 | 1.0 |
| 14 | 0.06 | 23.8 | 75.2 | 68.5 | 98.4 | 7.7 | 1.3 |
| 15 | 4.61 | 29.2 | 94.6 | 63.3 | 98.6 | 7.5 | 2.6 |
| 16 | 5.31 | 27.3 | 86.2 | 67.4 | 97.3 | 5.3 | 1.0 |
| 17 | 4.67 | 32.1 | 87.4 | 65.5 | 97.8 | 2.4 | 1.1 |
| 18 | 0.87 | 26.0 | 77.1 | 55.2 | 98.5 | 18.8 | 1.0 |
| 19 | 3.21 | 23.8 | 92.3 | 69.3 | 97.1 | 6.9 | 2.1 |
| 20 | 1.17 | 24.3 | 82.2 | 66.9 | 96.5 | 8.8 | 1.2 |
| 21 | 1.78 | 21.4 | 73.9 | 68.6 | 97.9 | 10.0 | 3.2 |

TABLE 3

Activities of the catalysts and product compositions of Examples 22-34 and Reference Example 1

| Examples | Activity ($10^6$ g/ (mol Cr · h)) | $C_6$ (wt %) | 1-$C_6$ in $C_6$ (%) | $C_8$ (wt %) | 1-$C_8$ in $C_8$ (%) | $C_{10+}$ (wt %) | PE (wt %) |
|---|---|---|---|---|---|---|---|
| 22 | 5.75 | 29.7 | 67.3 | 62.3 | 99.2 | 8.0 | 3.2 |
| 23 | 6.25 | 26.5 | 96.3 | 69.2 | 97.2 | 4.3 | 2.5 |
| 24 | 3.46 | 29.2 | 62.7 | 55.5 | 98.3 | 15.3 | 3.8 |
| 25 | 2.43 | 31.6 | 79.5 | 57.3 | 98.2 | 11.1 | 2.4 |
| 26 | 2.67 | 30.5 | 94.6 | 60.3 | 97.7 | 9.2 | 1.6 |
| 27 | 2.53 | 21.8 | 93.2 | 67.5 | 98.2 | 10.7 | 2.0 |
| 28 | 3.92 | 22.5 | 91.5 | 67.6 | 97.6 | 9.9 | 2.4 |
| 29 | 3.18 | 22.3 | 96.8 | 65.4 | 98.3 | 12.3 | 2.4 |
| 30 | 2.71 | 24.8 | 75.6 | 59.7 | 98.2 | 15.5 | 3.0 |
| 31 | 3.12 | 86.2 | 76.3 | 3.4 | 98.4 | 10.4 | 2.2 |
| 32 | 2.18 | 90.2 | 90.6 | 3.1 | 99.0 | 6.7 | 1.0 |
| 33 | 1.43 | 92.1 | 96.5 | 3.4 | 99.0 | 4.5 | 1.0 |
| 34 | 1.32 | 89.3 | 92.5 | 4.6 | 99.0 | 6.1 | 1.2 |
| Reference Example 1 | 0.38 | 59.8 | 68.0 | 30.2 | 100.0 | 10.5 | 50.9 |

The invention claimed is:

1. A chromium catalyst, which has a general formula as follows:

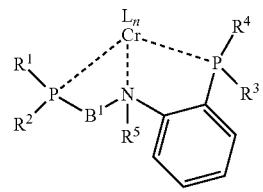

herein in above structure, $R^1$, $R^2$, $R^3$, $R^4$, and $R^5$ represent one of H, linear or branched alkyl, heteroalkyl, cycloalkyl, heterocycloalkyl, and aryl, $B^1$ represents one methylene group or a plurality of methylene groups, and Ln represents a group which has a chemical bond with metal chromium.

2. The chromium catalyst according to claim 1, wherein the chromium catalyst is formed by a chromium compound and an organic ligand containing P and N.

3. The chromium catalyst according to claim 1, wherein the $R^5$ group is one selected from the group consisting of H, $C_1$-$C_{10}$ linear or branched alkyl, heteroalkyl, cycloalkyl, alkenyl, alkyl, and phenyl; and the $R^1$, $R^2$, $R^3$, and $R^4$ groups are respectively one selected from the group consisting of $C_1$-$C_{10}$ linear or branched alkyl, and aryl.

4. The chromium catalyst according to claim 3, wherein the $R^5$ group is one selected from the group consisting of H, methyl, ethyl, propyl, isopropyl, butyl, isobutyl, tert-butyl, pentyl, cyclobutyl, cyclopentyl, cyclohexyl, 2-methylcyclohexyl, 2,6-dimethylcyclohexyl, adamantly, vinyl, allyl, phenyl, naphthyl, 2-methylphenyl, 2,4-6-trimethylphenyl, 3,5-dimethylphenyl, 3,5-dimethoxyphenyl, 3,5-di-tert-butylphenyl, 2-thienyl, 2-furanyl, 2-pyridyl, and 3-pyridyl; and the $R^1$, $R^2$, $R^3$, and $R^4$ groups are respectively one selected from group consisting of methyl, ethyl, butyl, phenyl (which is optionally connected to be condensed nucleus compound), 2-methylphenyl, 4-methylphenyl, 3,5-dimethylphenyl, 2-methoxyphenyl, 4-methoxyphenyl, 3,5-dimethoxyphenyl, 4-tert-butylphenyl, 3,5-di-tert-butylphenyl, 2-nitrophenyl, 4-nitrophenyl, 4-cyanophenyl, 3,4-(methylenedioxy)phenyl, 4-benzoylphenyl, 4-ethoxycarbonylphenyl, 4-trifluoromethylphenyl, 1-naphthyl, 4,4'-biphenyl, 3,5-di(phenyl)phenyl, 2-thienyl, 2-furanyl, 2-pyridyl, and 3-pyridyl.

5. The chromium catalyst according to claim 1, wherein the chromium comes from a chromium inorganic compound or a chromium organic compound;
   wherein the chromium inorganic compound is chromium dichloride or chromium trichloride; and
   wherein the chromium organic compound is one selected from the group consisting of chromium dichloride-tetrahydrofuran complex, chromium dichloride-toluene tetrahydrofuran complex, chromium trichloride-tetrahydrofuran complex, chromium dichloride-carbene complex, chromium trichloride-carbene complex, chromium acetylacetonate, chromium iris (2-ethylhexanoate), methyl chromium dichloride-tetrahydrofuran complex, triphenyl chromium-tetrahydrofuran, complex, dimethyl chromium-carbene complex, diethyl chromium-carbene complex, diphenyl chromium-carbene complex, and carbonyl chromium.

6. The chromium catalyst according to claim 1, which is included in a carrier.

7. The chromium catalyst according to claim 1, wherein the chromium catalyst has the structure as follows:

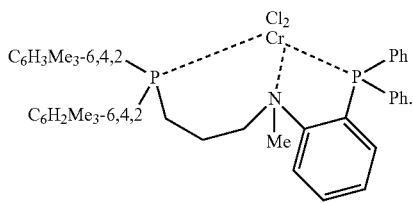

8. The chromium catalyst according to claim 1, wherein $B^1$ is —$CH_2CH_2CH_2$—.

9. The chromium catalyst according to claim 1, wherein each of $R^1$, $R^2$, $R^3$, and $R^4$ is phenyl.

10. An ethylene oligomerization method using the chromium catalyst of claim 1, comprising performing ethylene oligomerization reaction in the presence of the chromium catalyst.

11. The ethylene oligomerization method according to claim 10, wherein a reaction temperature ranges from 0° C. to 200° C., an ethylene pressure ranges from 0.1 MPa to 20 MPa, a reaction time ranges from 0.01 h to 200 h, and a concentration of the catalyst ranges from 0.001 mmol/L to 1000 mmol/L.

12. The ethylene oligomerization method according to claim 11, further comprising mixing the chromium catalyst with a co-catalyst in an organic solvent medium, so that a mixture obtained therein contacts with olefin and oligomerization reaction is performed.

13. The ethylene oligomerization method according to claim 12, wherein the co-catalyst is at least one selected from the group consisting of triethylaluminum, triisobutylaluminum, tri-n-butylaluminium, tri-n-hexylaluminium, tri-n-octylaluminium, methylaluminoxane, ethylaluminoxane, isobutylaluminoxane and modified aluminoxane, methylaluminoxane loaded on silica gel, alkylaluminum halide, tris (pentafluorophenol) aluminum, tris trifluoromethyl butanol) aluminum, triphenylmethyl-tetra (trifluoromethyl butanol) aluminum salts, tetrafluoroborate, ether tetrafluoroborate, epoxy borane, triethylborane, tris (pentafluorophenyl) borane, tetra (pentafluorophenyl) borate, tri-perfluoroaryl boranes, tetra-perfluoroaryl borate, tributyl borate, tetra (3,5-ditrifluoromethyl)phenyl borohydride salt, and tetra (3,5-ditrifluoromethyl) phenyl boron-sodium salts.

14. The ethylene oligomerization method according to claim 11, wherein a ratio of the chromium catalyst to the co-catalyst ranges from 1:10 to 1:4000.

15. The ethylene oligomerization method according to claim 12, wherein the co-catalyst is at least one selected from a group consisting of alkyl aluminum compound, aluminoxane compound, and organic boron compound.

16. The ethylene oligomerization method according to claim 12, wherein the organic solvent is at least one selected from the group consisting of toluene, xylene, n-butane, n-pentane, cyclopentane, methyl cyclopentane, n-hexane, n-heptane, cyclohexane, methylcyclohexane, tetrahydrofuran, dichloromethane, dichloroethane, ethyl ether, and isopropyl ether.

17. The ethylene oligomerization method according to claim 10, wherein the oligomerization comprises selective trimerization and tetramerization of ethylene so as to obtain 1-hexene and 1-octene.

18. The ethylene oligomerization method according to claim 10, wherein the chromium catalyst is formed by a chromium compound and an organic ligand containing P and N.

19. The ethylene oligomerization method according to claim 10, wherein the $R^5$ group is one selected from the group consisting of H, $C_1$-$C_{10}$ linear or branched alkyl, heteroalkyl, cycloalkyl, alkenyl, and phenyl; and
   the $R^1$, $R^2$, $R^3$, and $R^4$ groups are respectively one selected from the group consisting of $C_1$-$C_{10}$ linear or branched alkyl, and aryl.

20. The ethylene oligomerization method according to claim 10, wherein the $R^5$ group is one selected from the group consisting of H, methyl, ethyl, propyl, isopropyl, butyl, isobutyl, tert-butyl, pentyl, cyclobutyl, cyclopentyl, cyclohexyl, 2-methylcyclohexyl, 2,6-dimethylcyclohexyl, adamantly, allyl, phenyl, naphthyl, 2-methylphenyl, 2,4-6-trimethylphenyl, 3,5-dimethylphenyl, 3,5-dimethoxyphenyl, 3,5-di-tert-butylphenyl, 2-thienyl, 2-furanyl, 2-pyridyl, and 3-pyridyl; and
   the $R^1$, $R^2$, $R^3$, and $R^4$ groups are respectively one selected from the group consisting of methyl, ethyl, butyl, phenyl, 2-methylphenyl, 4-methylphenyl, 3,5-dimethylphenyl, 2-methoxyphenyl, 4-methoxyphenyl, 3,5-dimethoxyphenyl, 4-tert-butylphenyl, 3,5-di-tert-butylphenyl, 2-nitrophenyl, 4-nitrophenyl, 4-cyanophenyl, 3,4-(methylenedioxy) phenyl, 4-benzoylphenyl, 4-ethoxycarbonylphenyl, 4-trifluoromethylphenyl, 1-naphthyl, 4,4'-biphenyl, 3,5-di(phenyl) phenyl, 2-thienyl, 2-furanyl, 2-pyridyl, and 3-pyridyl.

21. The ethylene oligomerization method according to claim 10, wherein the chromium comes from a chromium inorganic compound or a chromium organic compound:

wherein the chromium inorganic compound is chromium dichloride or chromium trichloride; and wherein the chromium organic compound is one selected from the group consisting of chromium dichloride-tetrahydrofuran complex, chromium dichloride-toluene tetrahydrofuran complex, chromium trichloride-tetrahydrofuran complex, chromium dichloride-carbene complex, chromium trichloride-carbene complex, chromium acetylacetonate, chromium tris (2-ethyl-hexanoate), methyl chromium dichloride-tetrahydrofuran complex, triphenyl chromium-tetrahydrofuran complex, dimethyl chromium-carbene complex, diethyl chromium-carbene complex, diphenyl chromium-carbene complex, and carbonyl chromium.

22. The ethylene oligomerization method according to claim 10, wherein the chromium catalyst is included in a carrier.

23. The ethylene oligomerization method according to claim 10, wherein the chromium catalyst has the structure as follows:

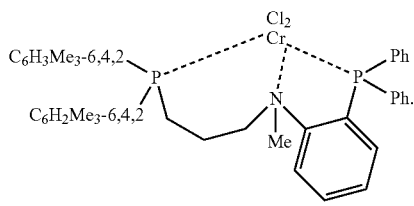

* * * * *

UNITED STATES PATENT AND TRADEMARK OFFICE
CERTIFICATE OF CORRECTION

| | |
|---|---|
| PATENT NO. | : 10,179,331 B2 |
| APPLICATION NO. | : 15/297904 |
| DATED | : January 15, 2019 |
| INVENTOR(S) | : Xianghong Zhong et al. |

It is certified that error appears in the above-identified patent and that said Letters Patent is hereby corrected as shown below:

On the Title Page

(73) listed in the Assignees section, "CHINA PETROLEUM & CHEIMCAL CORPORATION" should be -- CHINA PETROLEUM & CHEMICAL CORPORATION --

Signed and Sealed this
Twenty-third Day of April, 2019

Andrei Iancu
*Director of the United States Patent and Trademark Office*